US00PP32123P2

(12) United States Plant Patent
Van Swieten

(10) Patent No.: US PP32,123 P2
(45) Date of Patent: Aug. 25, 2020

(54) ***PHALAENOPSIS* ORCHID PLANT NAMED 'PHALGRYPS'**

(50) Latin Name: ***Phalaenopsis* hybrid**
Varietal Denomination: PHALGRYPS

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,199

(22) Filed: Aug. 27, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variety Database 20200320, retrieved on Mar. 25, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALGRYPS', particularly characterized by having white, dotted and striped flowers with dark red lips, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGRYPS'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGRYPS'.

The new *Phalaenopsis* plant is a product of a planned breeding program conducted by the inventor in Bleiswijk, the Netherlands. The objective of this breeding program was to create a new *Phalaenopsis* plant with numerous attractive white, dotted and striped flowers with dark red lips, suitable for potted plant production.

The new *Phalaenopsis* plant 'PHALGRYPS' is a result of cross-pollination made by the inventor in October 2009 in Bleiswijk, the Netherlands, of the proprietary female, or seed parent, *Phalaenopsis* hybrid '01-3335' (unpatented) with the proprietary male, or pollen parent, *Phalaenopsis* hybrid '01-3338' (unpatented).

The new *Phalaenopsis* was selected by the inventor as a single plant within the progeny of the stated cross-pollination in a controlled greenhouse in Bleiswijk, the Netherlands, in September 2012. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on April 26, 2018, by Applicant who obtained the subject matter disclosed directly from the inventor. 'PHALGRYPS' has not been made publicly available or sold anywhere in the world prior to the effective filing date of this application with the exception of sales or disclosures made one year or less before the effective filing date of this claimed invention by Applicant who obtained 'PHALGRYPS' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGRYPS' as a new and distinct variety of *Phalaenopsis* plant:

1) White, dotted and striped flowers with dark red lips;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
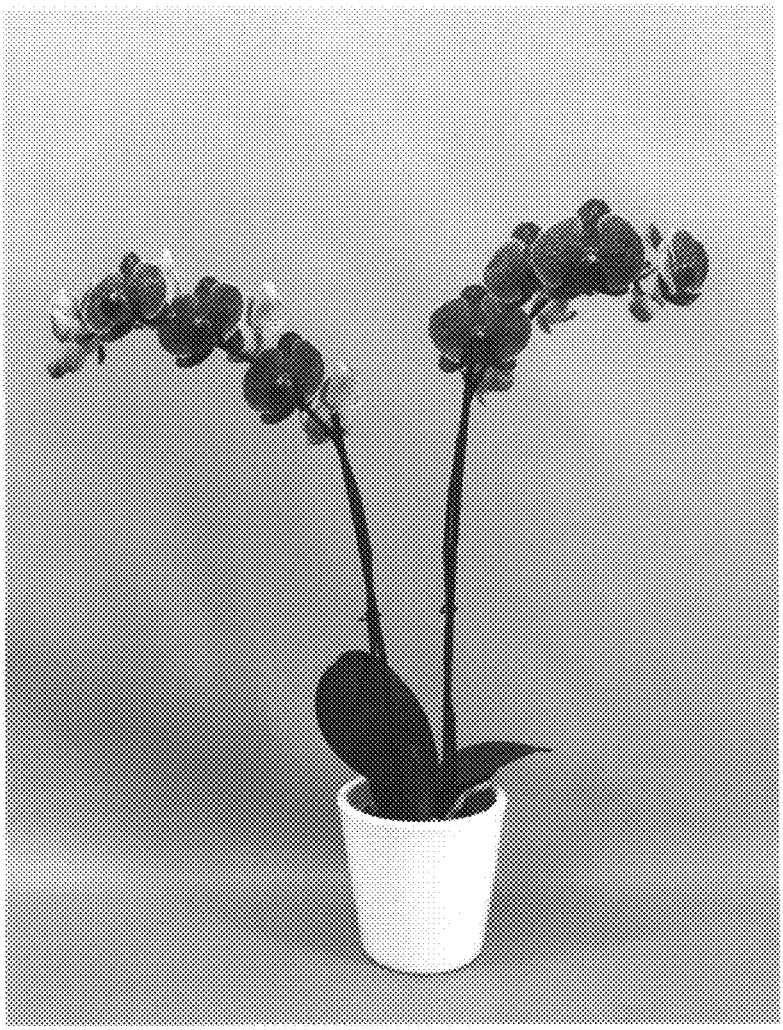
FIG. 1 shows the overall plant habit, including blooms, buds, and foliage of 'PHALGRYPS'.
Figure 2:
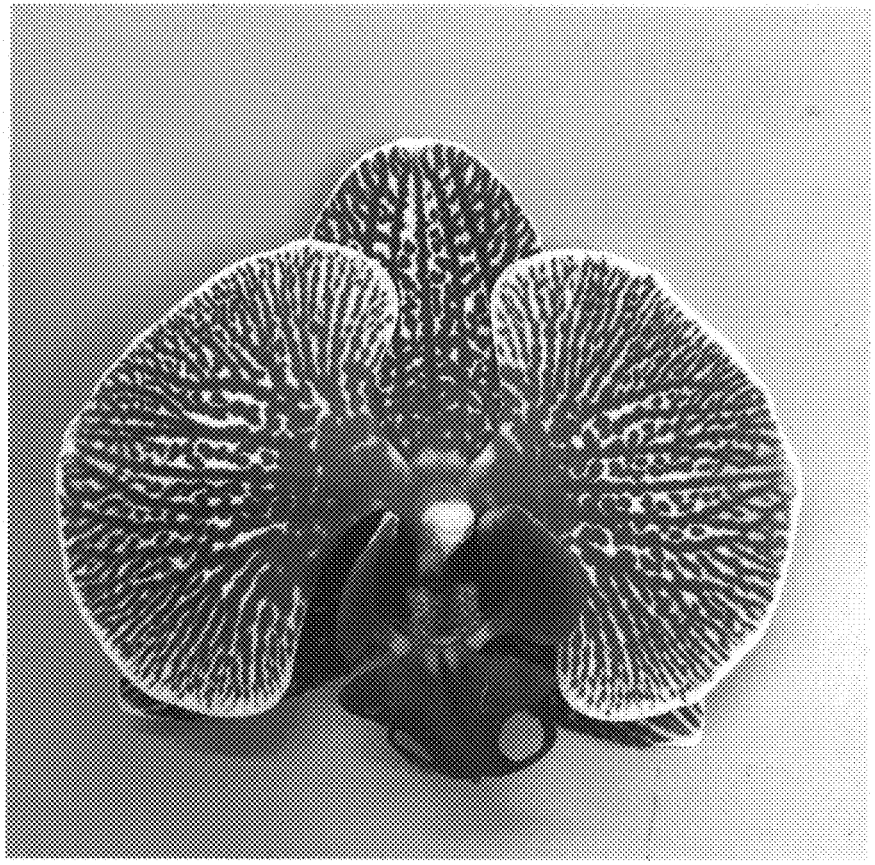
FIG. 2 shows a close-up of a flower of 'PHALGRYPS'.
Figure 3:
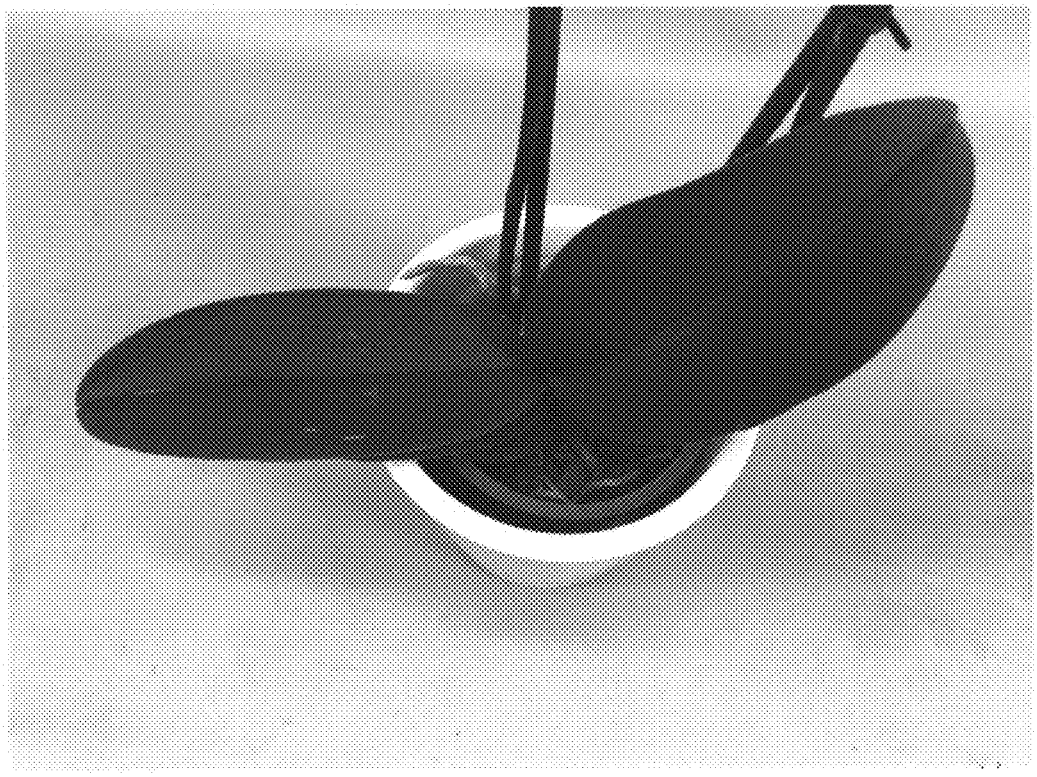
FIG. 3 shows an overhead view of the leaves of 'PHALGRYPS'.

The following detailed description sets forth the distinctive characteristics of 'PHALGRYPS'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALGRYPS'.

Parentage:

*Female parent.*—*Phalaenopsis* cultivar '01-3335' (unpatented).

*Male parent.*—*Phalaenopsis* cultivar '01-3338' (unpatented).

Propagation:

*Type.*—Meristem tissue culture.

Roots:

*Root description.*—Greyed-green (between RHS 190B and 190C) colored roots with branching lateral roots having light yellow-green (RHS 145C) colored root tips with a slight touch of RHS N77B.

Plant:

*Commercial crop time to flowering.*—Following asexual propagation (in-vitro), the rooted cuttings grow for 20 -24 weeks. After transplantation into 12-cm pots, the plants are finished after 48 to 50 weeks.

*Growth habit of peduncle.*—Upright to slightly pendant with raceme inflorescence.

*Height (from soil level to top of inflorescence).*—Approximately 55.0 cm to 60.0 cm.

*Width (measured from leaf tip).*—About 28.0 cm to 30.0 cm.

*Vigor.*—Moderate.

Leaves:

*Mature leaves.*—Quantity per plant: 6 to 8 leaves are produced before flowering. Length (fully expanded): 16.0 cm to 18.0 cm. Width: 7.0 cm to 8.0 cm. Shape: Oblong. Base shape: Moderately elongated. Apex: Obtuse unequal. Leaf blade angle with the petiole (measured from the horizontal position): Between 15 degrees and 30 degrees. Leaf margin: Entire. Color: Upper surface: RHS 147A. Lower surface: RHS 147B and diluting dark red (RHS 187A) toward margin. Spots (upper surface): Absent. Texture (both upper and lower surfaces): Slightly smooth. Thickness: 2.7 mm to 3.2 mm. Variegation: Absent. Venation: Pattern: Parallel. Color of the midvein: Upper surface: RHS 147A. Lower surface: RHS 147B.

Peduncle:

*Quantity per plant.*—1 to 2.

*Number of flowers per peduncle.*—8 to 12.

*Length.*—55.0 cm to 60.0 cm.

*Diameter.*—5.0 mm to 5.5 mm.

*Strength.*—Strong.

*Aspect.*—Upright to slightly pendant.

*Texture.*—Smooth.

*Color.*—Brown (RHS 200A) with a touch of yellow-green (RHS 146C).

*Internode length.*—4.0 cm to 5.0 cm.

Inflorescence description:

*Appearance.*—Upright to slightly pendant, raceme inflorescence with bilaterally symmetrical flowers that open in succession beginning with the lowermost flower.

*Number of inflorescences.*—1 to 2.

*Inflorescence size.*—Height (from base to tip): 200.0 mm to 250.0 mm.

*Flowering time.*—First flowers can be expected 10 to 11 months after planting in a 12-cm pot.

*Flower.*—Height: 74.0 mm to 79.0 mm. Diameter: 85.0 mm to 90.0 mm. Depth of lip: 25.0 mm to 27.0 mm.

*Flower longevity.*—On the plant: 9 to 13 weeks.

*Fragrance.*—Absent.

*Flower bud.*—Average size: Large. Length: 22.0 mm to 24.0 mm. Width: 20.0 mm to 22.0 mm. Shape: Egg shaped. Color: Yellow-green (RHS N144C).

*Petals.*—Arrangement: Open/free. Curvature at longitudinal axis: Recurving. Shape: Semi-circular. Shape in cross section: Convex. Presence of any twisting: Absent. Apex: Rounded asymmetric. Margin: Slightly undulated. Intensity of undulation of the margin: Weak. Length (from base to tip): 40.0 mm to 42.0 mm. Width: 56.0 mm to 58.0 mm. Position of the broadest part of the petal: Toward the base. Color (when fully opened): Upper surface: Basic color: White (RHS NN155C). Over color: Dark purplish-red (RHS N79C) at the base; dark red-purple dots and stripes (mix of RHS N79C and N78A). Number of dots and stripes: Many dots and many stripes. Size of dots and stripes: Medium dots and medium to large stripes. Lower surface: Basic color: Greenish-white (RHS 155C). Over color: Light yellow-green (RHS 145C) at the base; reddish-purple stripes (RHS N78B).

*Dorsal sepal.*—Curvature at longitudinal axis: Incurving. Shape: Elliptic. Shape in cross section: Concave. Presence of any twisting: Absent. Apex: Rounded symmetric. Margin: Entire. Intensity of undulation of the margin: Absent. Length (from base to tip):

45.0 mm to 47.0 mm. Width: 33.0 mm to 35.0 mm. Color (when fully opened): Upper surface: Basic color: White (RHS NN155C). Over color: Dark red-purple dots and stripes and base (mix of RHS N79C and N78A). Number of dots and stripes: Many dots and many stripes. Size of dots and stripes: Medium dots and medium to large stripes. Lower surface: Basic color: Greenish-white (RHS 155C). Over color: Light yellow-green (RHS 145D) with diluting reddish-purple stripes (RHS N78A to N78B) toward margin.

*Lateral sepals.*—Shape: Ovate. Apex: Obtuse asymmetric. Margin: Entire. Length (from base to tip): 43.0 mm to 45.0 mm. Width: 27.0 mm to 29.0 mm. Color (when fully opened): Upper surface: Basic color: White (RHS NN155C). Over color: Dark red (RHS 59A) at the base and dark purplish-red dots and stripes (RHS N79C). Number of dots and stripes: Many dots and many stripes. Size of dots and stripes: Medium. Lower surface: Basic color: Greenish-white (RHS 155C). Over color: Light yellow-green (RHS 145D) with diluting purplish-red stripes (RHS N77B) at the margin.

*Labellum* (*lip*).—Whiskers: Present. Length of whiskers: 21.0 mm to 23.0 mm. Color of whiskers: Dark red (RHS 187B). Pubescence on the lip: Absent.

*Lateral lobe.*—Shape: Type V (as described in the International Union for the Protection of New Varieties of Plants (UPOV) Test Guidelines for *Phalaenopsis*); spatulate. Curvature: Medium. Margin: Undulated. Length: 18.0 mm to 20.0 mm. Width: 15.0 mm to 17.0 mm. Color: Dark red (RHS 187B) at the base and on one side; reddish-purple (RHS 187C to 187D) toward other side; white margin (RHS NN155C) on one side. Number of stripes and netting: None. Fusion of the lateral lobes to the apical lobe: None.

*Apical lobe.*—Shape: Triangular. Margin: Entire. Length: 19.0 mm to 21.0 mm. Width: 23.0 mm to 25.0 mm. Color: Yellowish-green (RHS N144A) at the base and dark red (RHS 187B to 187C) toward whiskers. Number of spots, stripes, and netting: None.

*Callus.*—Average size: Large. Height: 6.0 mm to 7.0 mm. Length: 7.0 mm to 8.0 mm. Width: 5.0 mm to 6.0 mm. Color: Greenish-yellow (RHS 2A); dotted (RHS 59A).

Reproductive organs:

*Column.*—Length: 8.0 mm to 10.0 mm. Diameter: 5.0 mm to 6.0 mm. Color: Reddish-purple (RHS N78A to N78B).

*Pollinia.*—Quantity: 2. Diameter: 1.1 mm to 1.4 mm. Color: Orange (RHS 23A).

*Ovary.*—Length: 9.0 mm to 11.0 mm. Diameter: 2.6 mm to 2.9 mm. Color: Light yellow-green (RHS 145B) and very light purple (RHS 76C) toward the flower.

*Pedicel.*—Length: 35.0 mm to 37.0 mm. Diameter: 3.0 mm to 3.3 mm. Color: Yellow-green (RHS 145A).

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALGRYPS', cultivar '01-3335' (unpatented), is no longer in existence, therefore a meaningful comparison cannot be made.

The male parent plant of 'PHALGRYPS', cultivar '01-3338' (unpatented), is no longer in existence, therefore a meaningful comparison cannot be made.

'PHALGRYPS' is most similar to the commercial *Phalaenopsis* plants named 'PHALFLACAN' (U.S. Plant Pat. No. 27,910) and 'PHALBUKALO' (U.S. Plant Pat. No. 28,322). 'PHALGRYPS' differs from the commercial variety 'PHALFLACAN' in that 'PHALGRYPS' has spatulate lateral lobes, rounded petal apexes, and flowers with a dotted and striped pattern, whereas 'PHALFLACAN' has weakly spatulate lateral lobes, emarginated petal apexes, and flowers with a dotted pattern. Additionally, 'PHALGRYPS' has longer whiskers and wider petals than 'PHALFLACAN'.

'PHALGRYPS' differs from the commercial variety 'PHALBUKALO' in that 'PHALGRYPS' has rounded petal apexes and flowers with a dotted and striped pattern, whereas 'PHABUKALO' has slightly emarginated petal apexes and flowers with a striped and netted pattern. Additionally, 'PHALGRYPS' has longer whiskers and wider petals than 'PHALBUKALO'.

I claim:

1. A new and distinct variety of *Phalaenopsis* plant named 'PHALGRYPS', substantially as described and illustrated herein.

* * * * *